US00PP20412P2

(12) United States Plant Patent
Probst

(10) Patent No.: US PP20,412 P2
(45) Date of Patent: Oct. 13, 2009

(54) ***COREOPSIS* PLANT NAMED 'REDSHIFT'**

(50) Latin Name: ***Coreopsis* hybrid**
Varietal Denomination: Redshift

(76) Inventor: Darrell R. Probst, 63 Williamsville Rd., Hubbardston, MA (US) 01452-1315

( * ) Notice: Subject to any disclaimer, the term of this patent is extended or adjusted under 35 U.S.C. 154(b) by 0 days.

(21) Appl. No.: 12/286,714

(22) Filed: Oct. 1, 2008

(51) Int. Cl.
*A01H 5/00* (2006.01)

(52) U.S. Cl. ..... Plt./417
(58) Field of Classification Search ..... Plt./417
See application file for complete search history.

*Primary Examiner*—Susan B McCormick Ewoldt
(74) *Attorney, Agent, or Firm*—Penny J. Aguirre

(57) ABSTRACT

A new cultivar of hybrid *Coreopsis* named 'Redshift' characterized its large inflorescences that are light yellow in color with a burgundy red eye zone during the warm growing season with the ray florets becoming flushed with burgundy red to solid burgundy red when cool temperatures in fall, its sturdy stems, its vigorous growth habit, and its perennial habit and cold hardiness to at least to U.S.D.A. 5.

3 Drawing Sheets

Botanical classification: *Coreopsis* hybrid.
Variety denomination: 'Redshift'.

CROSS-REFERENCE TO A RELATED APPLICATION

This application is co-pending with a U.S. Plant patent application filed for a plant derived from the same cross in the inventor's breeding program that is entitled *Coreopsis* Plant Named 'Full Moon' (U.S. Plant patent application Ser. No. 11/982,547).

BACKGROUND OF THE INVENTION

The present invention relates to a new and distinct cultivar of *Coreopsis* plant, botanically of hybrid origin and known as *Coreopsis* 'Redshift' and will be referred to hereinafter by its cultivar name, 'Redshift'. The new cultivar of *Coreopsis* is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A Zone 5 in a wide range of flower colors and plant forms. The inventor collected seed in the wild from five different species that are not commercialized and made six generations of crosses to produced interspecific hybrids to utilize in his breeding work.

The inventor made a controlled cross in 2005 in his test garden in Hubbardston, Mass. between an unnamed F1 hybrid between *Coreopsis rosea* and an interspecific hybrid from his breeding program as the female parent and an unnamed plant of hybrid *Coreopsis* from his breeding program as the male parent. Neither parent is patented. 'Redshift' was selected in summer 2006 as a single unique plant amongst the resulting seedlings.

Asexual reproduction of the new cultivar was first accomplished by stem cuttings in a controlled environment in Hubbardston, Mass. in July of 2006 by the inventor. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Redshift' as unique from all *Coreopsis* cultivars and species known to the inventor.

1. 'Redshift' exhibits large composite inflorescences up to 6.3 cm (2.5 inches) in diameter.
2. 'Redshift' exhibits composite inflorescences that are light yellow in color with a burgundy red eye zone during the warm growing season with the ray florets becoming flushed with burgundy red to solid burgundy red when cool temperatures in fall.
3. 'Redshift' exhibits sturdy stems.
4. 'Redshift' exhibits a vigorous growth habit.
5. 'Redshift' is cold hardy at least to U.S.D.A. Zone 5.

'Redshift' differs from its female parent in that the female parent has weaker stems, a more lax plant habit and flowers that are smaller and pale yellow in color. The male parent differs from 'Redshift' in having dark golden yellow flowers with a much shorter blooms period. 'Redshift' can be compared to *Coreopsis* 'Full Moon' and *Coreopsis* Crème Brulee' (U.S. Plant Pat. No. 16,096). 'Redshift' is similar to 'Full Moon' in flower size and growth habit, however 'Full Moon' differs from 'Redshift' in having brighter yellow flowers that lack the burgundy red coloration of 'Redshift'. 'Redshift' is similar to Crème Brulee' in having light yellow flowers, however 'Redshift' differs from Créme Brulee' in having larger flowers with burgundy red coloration, a much sturdier plant habit, and in having a true perennial growth habit in U.S.D.A. Zone 5.

BRIEF DESCRIPTION OF THE DRAWING

The accompanying colored photographs illustrate the overall appearance and distinct characteristics of the new *Coreopsis*. The photographs in FIG. 1, FIG. 2, and FIG. 3 were taken of two year-old plants of 'Redshift' as grown in the Inventor's garden in Hubbardston, Mass.

The photograph in FIG. 1 shows the overall growth habit in summer.

Figure 1:
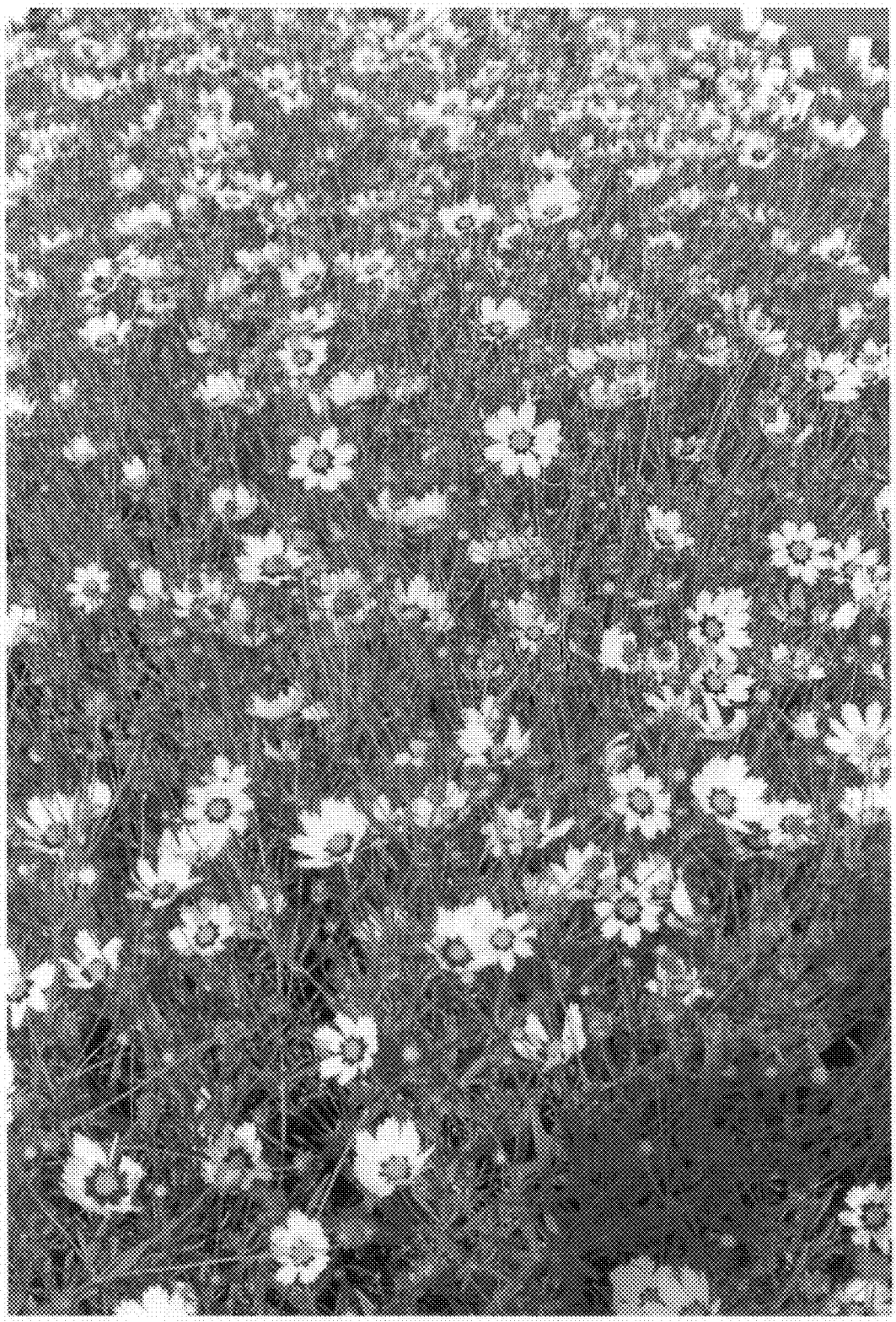
Figure 2:
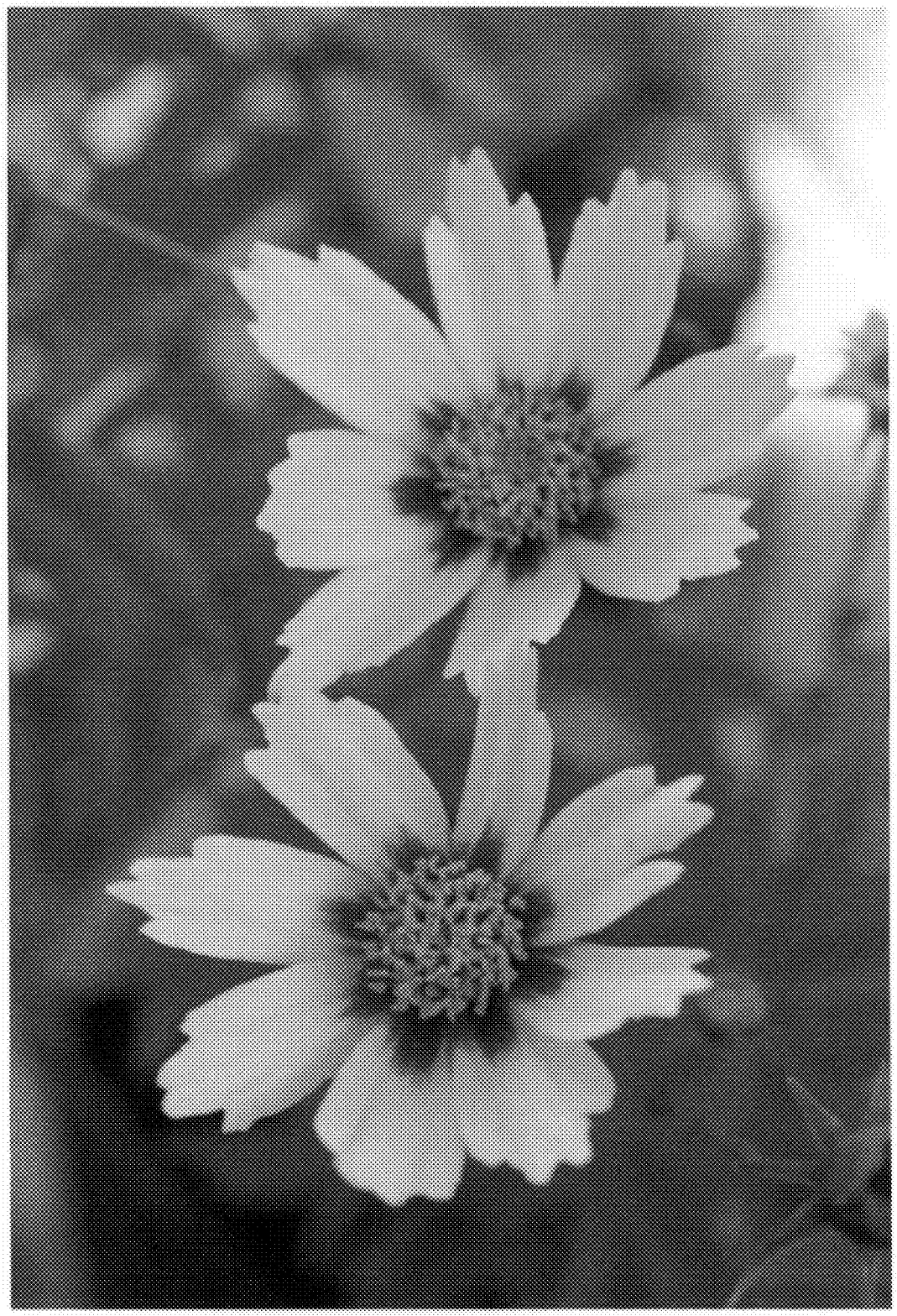

The photograph in FIG. 2 provides a close-up view of inflorescences of 'Redshift' in mid summer.

Figure 3:
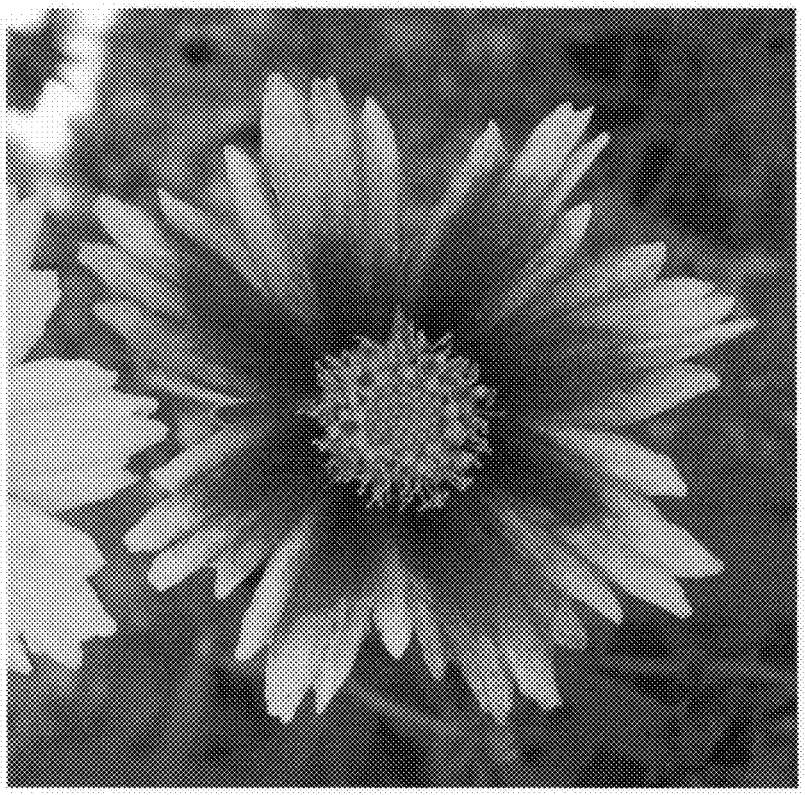

The photograph in FIG. 3 provides a close-up view of a typical inflorescence of 'Redshift' in fall with cooling temperatures.

Figure 4:
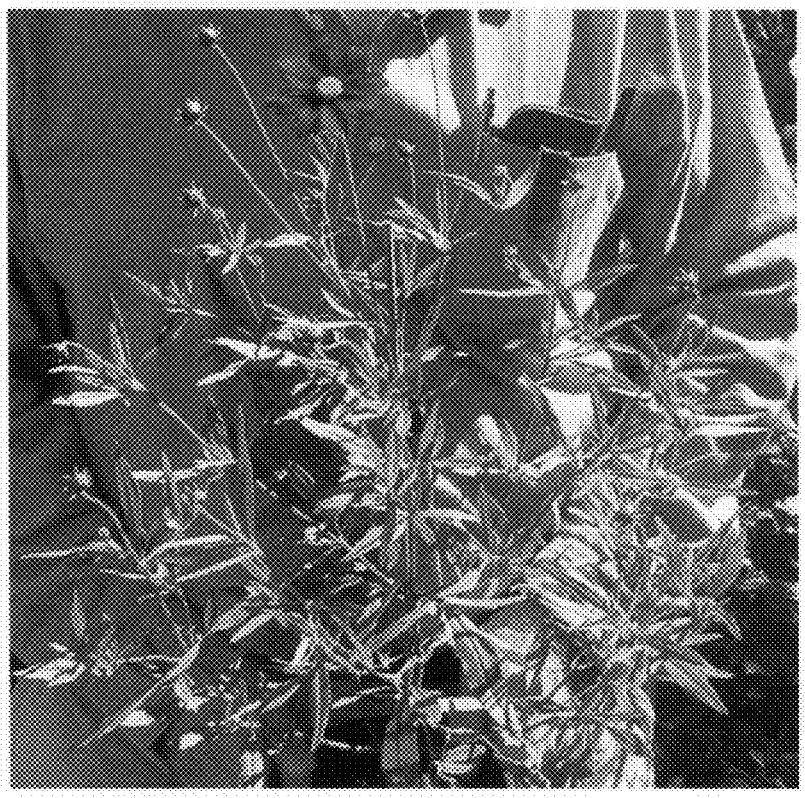

The photograph in FIG. 4 was taken of a six-month old plant of 'Redshift' as grown in a one-gallon container in Hubbardston, Mass. and provides a view of an inflorescence of 'Redshift' in fall that has turned solid burgundy red.

The Colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for two years in a trail garden in Hubbardston, Mass. with the detailed botanical data collected from a six month-old plant of the new cultivar as grown in a one-gallon container as grown outdoors in Kensington, Conn. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period.*—Blooms from late July until frost in central Massachusetts.

*Plant habit.*—Herbaceous perennial, clump-forming with canopy upright and spreading with sturdy stem.

*Height and spread.*—Reaches 60 to 76 cm (24 to 36 inches) in height and 76 to 91 cm (30 to 36 inches) in width when mature.

*Cold hardiness.*—At least to U.S.D.A Zone 5, has not been tested in colder regions.

*Diseases resistance.*—More resistance to powdery mildew has been observed in comparison to other large flowered *Coreopsis* cultivars (*Coreopsis grandiflora*) grown under the same conditions.

*Root description.*—Fibrous, fine and well-branched.

Growth and propagation:

*Propagation.*—Terminal stem cuttings and division.

*Growth rate.*—Vigorous.

Stem description: *Coreopsis* Redshift

*Shape.*—Tetragonal, solid.

*Stem color.*—146A.

*Stem size.*—Main stem averages 36 cm in length with laterals an average of 15 cm in length (excluding peduncles), an average of 2.5 mm in width.

*Stem surface.*—Glabrous when young, ridged and sparsely covered with minute translucent hairs when mature.

*Branching habit.*—An average of 12 basal branches with 1 to 5 secondary branches, branch internode is variable but typically about 7 cm and arise opposite at nodes.

Foliage description:

*Leaf division.*—Simple.

*Leaf margins.*—Primarily entire with some leaves having one secondary lobe often held nearly horizontal to primary lobe, covered with short hairs and slight undulations.

*Leaf size.*—Up to 9 cm in length and 1.5 cm in width secondary lobe up to 4 cm in length and 5 mm in width.

*Leaf shape.*—Lanceolate with secondary lobes lanceolate.

*Leaf base.*—Attenuate.

*Leaf apex.*—Narrowly acute.

*Leaf venation.*—Pinnate, not prominent, coloration same as leaf with base on both surfaces 144B.

*Leaf attachment.*—Sessile.

*Leaf arrangement.*—Opposite.

*Leaf surface.*—Dull and very finely puberulent on upper surface and lower surface.

*Leaf color.*—Young upper surface; 137B, young lower surface; 147B, mature upper surface; N137A, mature lower surface; a blend of 146A and 137A.

Flower description:

*Inflorescence type.*—Composite with ray florets surrounding disk florets in the center, forming a radiant head, inflorescences are borne on terminals arising from leaf axils.

*Lastingness of inflorescence.*—About one week until senescence of ray flowers, bracts and disk flowers are persistent.

*Fragrance.*—None detected.

*Quantity of inflorescences.*—An average of 6 per lateral branch, an average of 124 per plant grown in a one-gallon container.

*Inflorescence size.*—Average 1.2 cm in depth and up to 6.3 cm in diameter with disk portion up to 1.1 cm in diameter.

*Inflorescence buds.*—Average of 9 mm in depth and diameter, shape is spherical, color is 7A covered with bracts 146A to 146B in color.

*Peduncle.*—Strong, average of 9 cm in length and 1.5 mm in diameter, 138A in color, glabrous surface.

Involucral bracts:

*Bract number.*—Two rows of 8.

*Bract arrangement.*—Outer bracts are un-fused and somewhat reflexed when flower is fully open and becoming horizontal after ray florets drop, inner bracts overlap and surround receptacle with a campanulate form with apical portion un-fused, spreading, and held close to ray florets.

*Bract size.*—*Outer bracts about* 6 mm in length and 2 mm in width, inner bracts about 1 cm in length and 3 mm in width with free portion an average of 6 mm in length and 3 mm in width.

*Bract color.*—Outer bracts 138A in both surfaces, inner bracts; fused portion 147B, unfused portion 147B in center with apex and margin 15B.

*Bract texture.*—Outer bract; puberulent, inner bracts waxy.

*Bract apex.*—Outer bract; narrowly acute, inner bracts; apiculate.

*Bract base.*—Truncate.

*Bract shape.*—Outer bracts; lanceolate, inner bracts; free portion broadly lanceolate.

Ray florets (sterile):

*Number.*—8.

*Shape.*—Oblong, appearance of three longitudinal sections with center section longer.

*Size.*—Average of 2.1 cm in length and 1 cm in width.

*Apex.*—Emarginate with 3 notches.

*Base.*—Broadly cuneate.

*Margins.*—Entire on sides, notched on apex.

*Aspect.*—Held slightly cupped upward.

*Texture.*—Glabrous on both surfaces.

*Color.*—Upper surface when fully open warm temperatures; 5B to 5C with a spot of 59A at base in warm temperatures, lower surface when fully open in warm temperatures; 5B to 5C, upper surface when fully open in cool temperature; 7B and heavily suffused with 59A to 59B to solid 59A, lower surface when fully open in cool temperature; 7B with very narrow margin of 59A and diffused with 59A when upper surface is solid 59A.

Disk flowers (male and female):

*Shape.*—Tubular, corolla is fused, flared at apex.

*Size.*—About 6 mm in length and 1.3 mm in width.

*Color.*—In masse; 153A when immature, 17B when fully open and becoming 200D when dried and ray florets drop, corolla; base (tube) is 144D in color, flared portion is 17D and translucent.

*Receptacle.*—About 4 mm in diameter and 2 mm in depth, 144D in color.

Reproductive organs:

*Presence.*—Disk flowers are perfect, ray flowers are sterile.

*Gynoecium.*—1 Pistil, 4 mm in length, style is very fine and about 152D in color and translucent, bifid pilose stigma is 17B in color with branches about 1.5 mm in length and recurved, ovary is 2 mm in length, 1 mm in width, inferior, and 145D in color.

*Androcoecium.*—5 stamens, fused into tube surrounding style, 3 mm in length and 0.7 mm in width, about 165A in color, no pollen was observed.

*Fruit/seed.*—No fruit or seed development was observed.

The invention claimed is:

1. A new and distinct cultivar of *Coreopsis* plant named 'Redshift' as herein illustrated and described.

* * * * *